US005534019A

United States Patent [19]

Paspa

[11] Patent Number: 5,534,019
[45] Date of Patent: Jul. 9, 1996

[54] CARDIAC DEFIBRILLATOR WITH CASE THAT CAN BE ELECTRICALLY ACTIVE OR INACTIVE

[75] Inventor: Paul M. Paspa, Santa Clara, Calif.

[73] Assignee: Ventritex, Inc., Sunnyvale, Calif.

[21] Appl. No.: 353,422

[22] Filed: Dec. 9, 1994

[51] Int. Cl.$^6$ .................................................. A61N 1/375
[52] U.S. Cl. ............................................................ 607/38
[58] Field of Search ................................ 607/2, 5, 36–38, 607/119, 148

[56] References Cited

U.S. PATENT DOCUMENTS

| | | |
|---|---|---|
| 3,951,154 | 4/1976 | Hartlaub . |
| 4,301,805 | 11/1981 | Peers-Trevarton et al. . |
| 4,310,000 | 1/1982 | Lindemans ................................ 607/38 |
| 4,727,877 | 3/1988 | Kallok . |
| 4,907,592 | 3/1990 | Harper . |
| 4,922,927 | 5/1990 | Fine et al. . |
| 5,133,353 | 7/1992 | Hauser ........................................ 607/9 |
| 5,174,288 | 12/1992 | Bardy et al. . |
| 5,220,929 | 6/1993 | Marquit ................................ 607/36 X |
| 5,261,400 | 11/1993 | Bardy ....................................... 607/5 |
| 5,261,411 | 11/1993 | Hughes ................................... 128/668 |
| 5,374,279 | 12/1994 | Duffin, Jr. et al. ......................... 607/5 |
| 5,376,103 | 12/1994 | Anderson et al. ........................... 607/5 |
| 5,447,521 | 9/1995 | Anderson et al. ........................... 607/5 |

OTHER PUBLICATIONS

"Cardiac Pacemakers, Part 3: Low–Profile Connectors (IS–1) for Implantable Pacemakers", *ISO* 5841–3 First Edition, 1992–Dec.–01, pp. i–9.

"Cardiac Defibrillators—Connector Assembly for Implantable Defibrillators—Dimensional and Test Requirements", *ISO* 11318:1993(E), pp. 1–19.

"Low–energy Endocardial Defibrillation Using an Axiallary or a Pectoral Thoracic Electrode Location", Saksena, et al., *Circulation*, vol. 88, No. 6, Dec. 1993, pp. 2655–2660.

Primary Examiner—William E. Kamm
Assistant Examiner—Jeffrey R. Jastrzab
Attorney, Agent, or Firm—Steven M. Mitchell; M. Elizabeth Bush; Mark J. Meltzer

[57] ABSTRACT

A defibrillator having a housing for enclosing and containing defibrillation pulse generator circuitry, particularly adapted to allow for ease of manufacture and use. At least one surface of the housing is electrically conductive and connected to the defibrillation pulse generator circuitry for delivering defibrillating energy to the heart. The defibrillator is provided with a case-activating lead connector cavity having two isolated conductive elements. By tightening a first setscrew onto a lead connector pin, an electrode of the lead becomes active. Tightening a second setscrew activates the can. Tightening both setscrews onto a plug pin activates the can alone. To use neither a lead in the case-activating port, nor an active can, only one setscrew may be tightened onto a conductive or nonconductive pin to plug the cavity without activating the can. By using this system, various electrode configurations can be used as required to provide the optimum system for a given patient. The defibrillator generator housing is preferably implanted in the left pectoral region proximate the heart with the conductive surface facing the heart. Other implantable electrodes are discharged against the defibrillator generator housing electrode.

20 Claims, 7 Drawing Sheets

1

CARDIAC DEFIBRILLATOR WITH CASE THAT CAN BE ELECTRICALLY ACTIVE OR INACTIVE

FIELD OF THE INVENTION

The present invention relates generally to implantable cardiac stimulation devices, and more specifically to a cardiac defibrillator with a case that is either electrically activated or left inactive at the time of implant.

BACKGROUND OF THE INVENTION

There has been substantial work directed towards development of implantable defibrillation systems that avoid the necessity of a thoracotomy. Systems that deliver a defibrillation pulse between one or more endocardial electrodes and an active defibrillator housing are disclosed in U.S. Pat. Nos. 4,727,877 issued to Kallok; 4,922,927 to Fine et al.; 5,133,353 to Hauser; and 5,261,400 to Bardy, all of which are incorporated herein by reference. As used herein, the words "housing", "enclosure", "case", and "can" are synonymous.

If a device is chosen to have an active can and is placed pectorally, it is unlikely that this decision would be changed in the future. If a lead is used subcutaneously and the inactive can implanted abdominally, it is again unlikely that there would be reason to change this, to "activate the can". Even if this decision were reversed, a surgical procedure would likely be required to reposition the can for effective use as an electrode. Therefore, external programmability of this choice of active or inactive can is not needed, allowing the design and manufacture to be somewhat less complex.

Thus, while it is desirable to have a choice of having the device housing function as an active electrode, this choice will almost always be made at the time of device implant, avoiding the need for added device complexity of having the choice be programmable after implant.

In the invention of Pless et al., U.S. Pat. application Ser. No. 08/221,811, filed Mar. 31, 1994, which is assigned to the assignee of the invention, a cardiac defibrillator with a case that can be electrically active or inactive is disclosed. A special connector cavity is provided that has one terminal electrically connected to the generator case and a second terminal connected to one pole of the defibrillator output. By plugging in a pin long enough to contact both terminals, the case is activated during a defibrillation shock. No means is disclosed for using a standard connector pin, such as a DF-1 defibrillator connector pin. Because of the desire to be compatible with existing lead connectors without requiring a special adapter, both at initial implant and during a pulse generator replacement, it would be useful if the pulse generator case could be activated using only a standard lead connector.

SUMMARY OF THE INVENTION

The present invention is directed toward the provision of a defibrillator that delivers a defibrillation pulse either between at least one transvenous lead electrode and at least a portion of the metal enclosure of the defibrillator, or between at least one transvenous lead electrode and an additional implanted lead located either transvenously, epicardially, or subcutaneously. The decision to use either the pulse generator case as an electrode, or to implant an additional lead, that is, whether the defibrillator can is electrically active or passive, is made by the implanting surgeon at the time of implant.

The defibrillator of the present invention is provided with a case-activating lead connector cavity having two conductive elements, each comprising a setscrew. By plugging in a lead and tightening the first setscrew but not the second, the lead becomes active. When both setscrews are tightened, both the lead and the can are active. Tightening both setscrews onto a plug activates only the can. In the case when neither a lead nor an active can is desired, tightening only one of the setscrews onto a plug with a conductive or nonconductive pin will mechanically stabilize the plug in the cavity without electrically activating the can.

By using the present invention, various electrode configurations can be used as required to provide the optimum system for a given patient without having to bring two defibrillators into the operating room, one having an active can and one having an inactive can, and without requiring any programmability from the manufacturer or programming by the physician. This invention also allows the use of standard lead connectors without requiring a special adapter or a lead having a special connector.

It is thus a primary object of this invention to provide an implantable cardiac stimulation system having defibrillation capabilities with a selectable electrode configuration.

It is an additional object of this invention to provide an implantable cardiac stimulation system that is simpler to implant than prior art systems.

It is a further object of this invention to provide an implantable cardiac stimulation system that can be used with previously implanted defibrillation leads.

It is yet a further object of this invention to provide an implantable cardiac stimulation system that is safer to manufacture and safer to implant.

BRIEF DESCRIPTION OF THE DRAWINGS

The various features and advantages of the present invention may be more readily understood with reference to the following detailed description taken in conjunction with the accompanying drawings in which.

DETAILED DESCRIPTION OF THE INVENTION

The invention will now be discussed in connection with the alternative choices it allows a surgeon to make at the time of implant of an implantable defibrillator. The decision to use either the pulse generator case as an electrode or to implant an additional lead, that is, whether the pulse generator can is electrically active or passive, is made by the implanting surgeon at the time of implant. The following are two examples of the many possible sequences of events in the decision making process:

EXAMPLE 1 a.) The defibrillation threshold (DFT) is found to be too high using only two transvenous electrodes, right ventricular (RV) and superior vena cava (SVC), even after reversing polarities.

b.) The defibrillator housing is activated for use as a subcutaneous (SQ)+ electrode in a midaxillary position, with RV− and SVC+. The DFT is acceptable.

EXAMPLE 2 a.) The DFT is found to be too high using only two electrodes, with an RV electrode negative (−) and an SVC electrode positive (+).

b.) Various attempts are made to lower the DFT, such as repositioning the SVC electrode, reversing polarity, and changing pulse width. The DFT is still too high.

c.) A subcutaneous (SQ) electrode is desired for location on the left chest wall. However, it is determined that the patient is too thin in the pectoral region for the defibrillator generator to be implanted there, and thus its housing cannot be used as an electrode.

d.) A separate SQ electrode is implanted in the desired location. The DFT is found to be acceptable using RV−, SVC+, and SQ+.

e.) The inactive pulse generator is implanted in the abdominal region.

EXAMPLE 3 a.) The DFT is found to be too high using RV− and SVC+.

b.) The pulse generator housing is used as a SQ+ electrode in a midaxillary position, with RV− and SVC+. The DFT is still too high.

c.) Attempts are made to lower the DFT by repositioning the SQ pulse generator housing, such as by moving it more anterior or posterior. The DFT is still too high.

d.) The polarity is changed to make RV+, SVC−, and SQ−. The DFT is acceptable.

Figure 1:
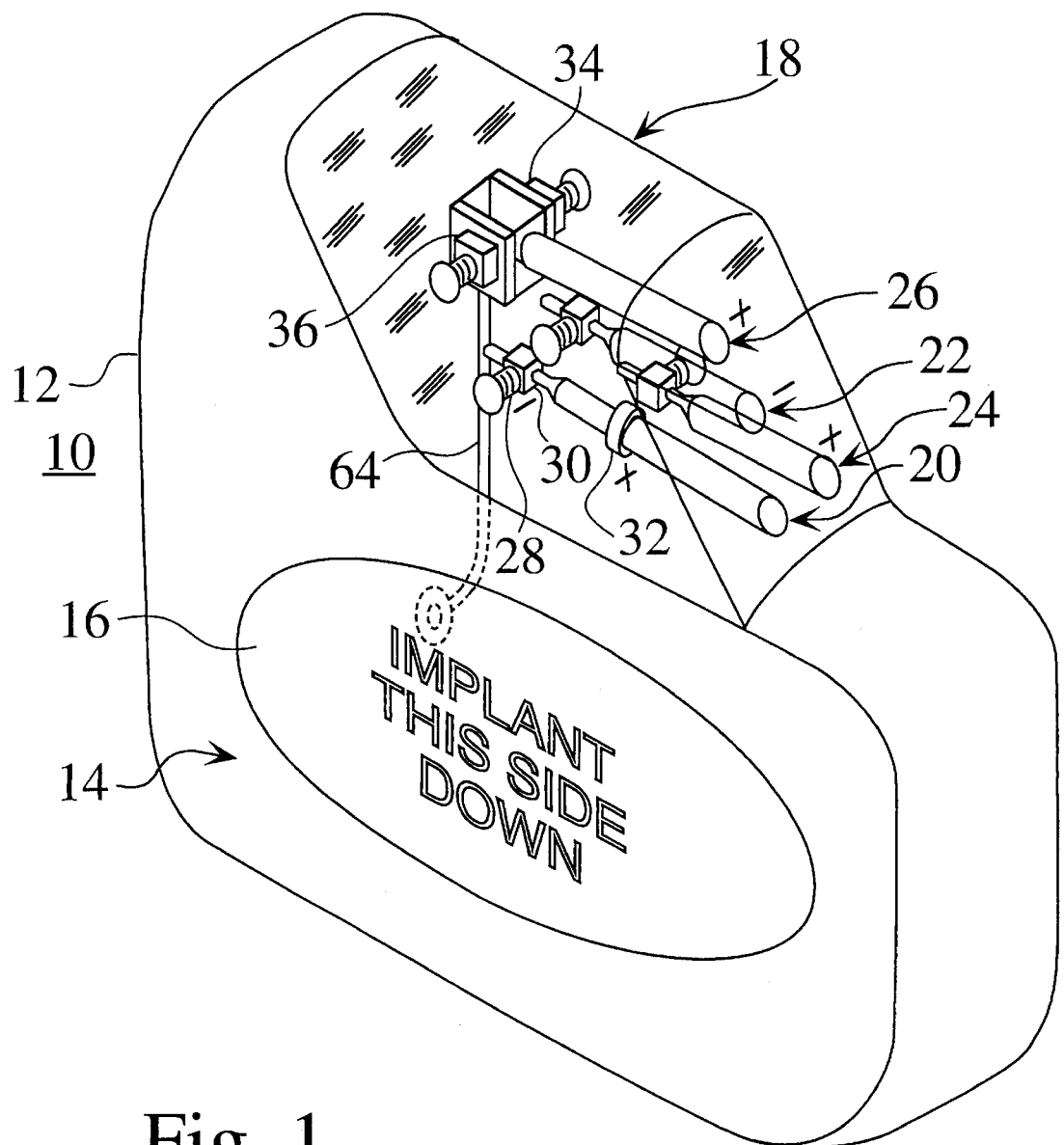
FIG. 1 illustrates the implantable defibrillator according to the present invention.

FIG. 1 illustrates an implantable pulse generator 10 according to the present invention. The defibrillator may have bradycardia and antitachycardia pacing capabilities as well as cardioversion and defibrillation capabilities. The housing 12 of the pulse generator 10 is typically titanium, although other corrosion resistant metals may be used. It is partially insulated by a polymeric coating 14, and has an exposed, conductive portion 16 which may serve as an electrode. The polymeric insulating coating 14 serves to keep current flow between electrodes focused toward the heart during a defibrillation shock, so as to lower defibrillation thresholds and to avoid unwanted skeletal muscle stimulation. Alternatively, the entire housing outer surface may be left uncoated, and therefore conductive. The outer surface of the pulse generator may be of a special configuration to facilitate its discharge capabilities. Alternative means for insulating the can may be used, such as an insulative biocompatible boot having a cutout.

A header 18, which is preferably made of transparent or translucent polymeric material, such as epoxy, polyurethane, or silicone rubber, contains four lead connector cavities 20, 22, 24, and 26. Alternatively, the header 18 may be built into the housing 12, or may be made of an opaque material; however, this is not preferred since the cavities would not be visible. The connector cavities shown are a bipolar pacing lead connector cavity 20, and three unipolar defibrillator connector cavities, two being of the standard type known in the art, and one of a special, case activating type which will be described in detail below.

The pacing lead connector cavity 20 has setscrew threads 28 to a connector block 30 for making a mechanical and electrical connection to a pacing lead connector pin, and a garter spring 32 for making an electrical connection to a pacing lead connector ring. Alternatively, other connector mechanisms may be used to electrically and mechanically connect the pin and ring to the pulse generator, such as a setscrew connection instead of the garter spring, or the "Collet Grip Connector Block" described in U.S. patent application Ser. No. 08/168,889 to Chris Julian, which i assigned to the assignee of the present application and is incorporated herein by reference. The pacing pin electrical connection 30 is negative in polarity, and the ring connection 32 is positive. The pacing lead connector cavity 20 may be of the IS-1 BI type described in ISO 5841-3:1992(E) "Cardiac pacemakers—Part 3: Low-profile connectors (IS-1) for implantable pacemakers" (International Standard). Alternatively, the header may include a pair of pacing lead connector cavities for use with two lead connectors of a bipolar bifurcated lead, or other configurations, as are well known in the art.

The standard defibrillation lead connector cavities 22 and 24 are of opposite polarity, and are designed for high energy defibrillation pulses. They may be of the DF-1 type described in ISO 11318:1993(E) "Cardiac defibrillators-Connector assembly for implantable defibrillators—Dimensional and test requirements" (International Standard). Again, block and setscrew connections are shown, but any suitable connection mechanism known in the art may be used for the connector cavity conductive element, which interfaces with the lead connector pin to form the current-carrying connector contact.

Figure 4:
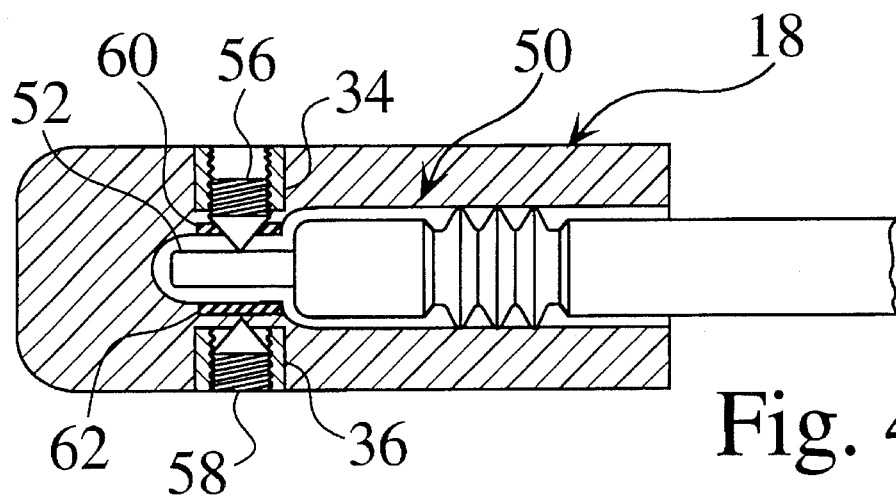
FIG. 4 is a top plan view partially cut away showing a connector assembly having the two connector blocks of the case-activating connector cavity of FIG. 1, and having a lead inserted and activated.
Figure 5:
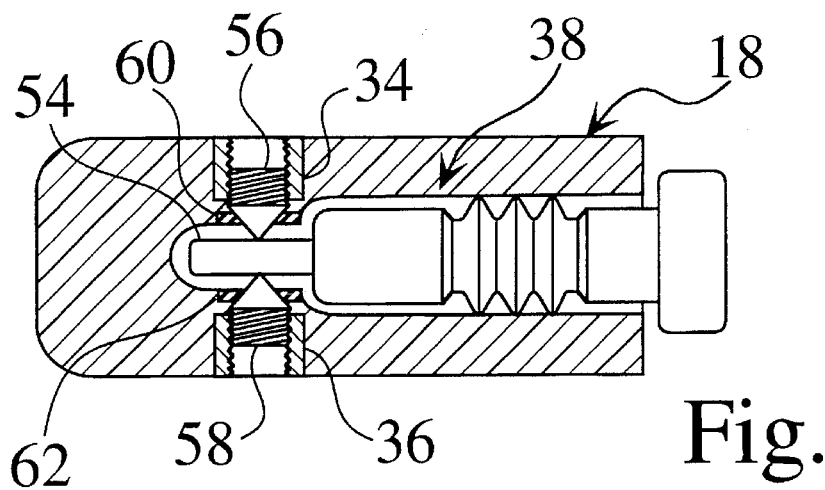
FIG. 5 is a top plan view partially cut away showing the two connector blocks of the case-activating connector cavity of FIG. 1, with a plug inserted and the can activated.
Figure 6:
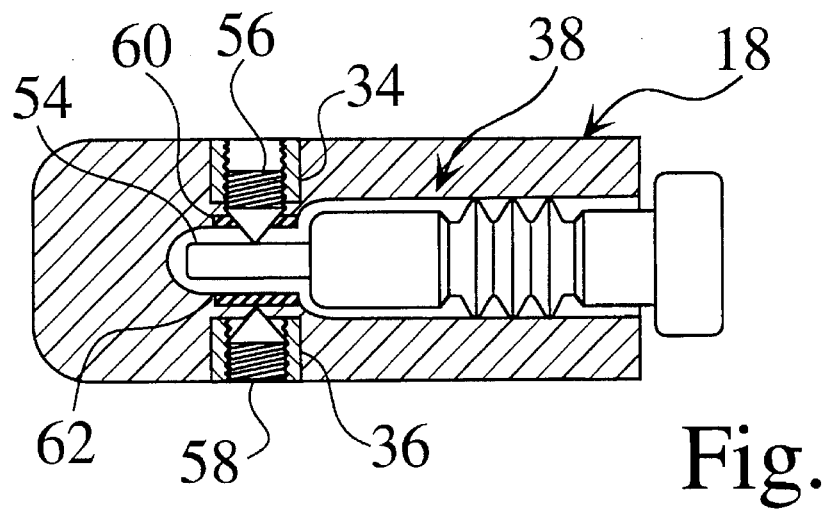
FIG. 6 is a top plan view partially cut away showing the two connector blocks of the case-activating connector cavity of FIG. 1, having a plug to fill the cavity but not activate the can.

The case-activating defibrillation connector cavity 26 has first and second conductive elements 34 and 36, shown as two connector blocks with setscrews. Other electrical connection mechanisms could alternatively be used for the connector cavity conductive element to interface with the lead connector pin to form the current-carrying connector contact. The first conductive element 34 is coupled to a positive terminal of the defibrillator generator circuitry (not shown). The second conductive element 36 is electrically coupled to the conductive portion 16 of the defibrillator case 12 by conductor 64. Plugging in a lead connector and tightening only the first setscrew 56, but not the second setscrew 58, onto the lead connector pin, as shown in FIG. 4, will activate the electrode attached to the lead connector pin, making it positive during a defibrillation shock. For activating the can alone, a plug 38 is inserted and both setscrews are tightened onto the plug pin as shown in FIG. 5. To seal off the case-activating port without activating the case, either setscrew, but not both, may be tightened onto a plug pin to mechanically stabilize it, as shown in FIG. 6. Because only one setscrew is tightened, the plug may have a conductive or nonconductive pin.

Connector cavity 26 may have the internal dimensions specified in ISO 11318:1993(E), which accepts a "DF-1" connector pin of about 5 mm in length. Conductive elements 34 and 36 may or may not be located at the same distance from the cavity entrance, but must be at least within the connector pin length from each other; in the case of a DF-1 connector, within 5 mm of each other. Conductive elements 34 and 36 may be located about 180° apart as shown in the FIGS. 1, and 4–7; alternatively, they may be spaced about the cavity perimeter by any number of degrees. For example, the conductive elements 34 and 36 of FIG. 1 may be located 90° apart, with one setscrew driven from the side of header 18 and the other setscrew driven from the top of header 18.

By using the system of the present invention, various electrode configurations can be used as required to provide the optimum system for a given patient without having to bring two defibrillators into the operating room, one active and one inactive, and without requiring any programmability from the manufacturer or programming by the physician.

Another advantage provided by the defibrillator of the present invention is realized both during manufacture and during handling by implanting medical personnel. In a system having a permanently active can, or one that can be conventionally programmed to be active or inactive, there is the danger that the defibrillator generator could deliver a high voltage shock to anyone handling the device during manufacture or implant, because it is impossible to tell by visual inspection whether such a system is turned on, thus requiring interrogation using a programmer or similar method. On the other hand, the defibrillator generator case of the present invention is not active unless a plug or lead is inserted in the case-activating cavity (and the setscrew tightened) as can be easily noted by visual inspection. Simply by not inserting this plug, the defibrillator case remains inactive throughout the manufacturing process. During implant, the plug need not be inserted until near the end of the implant procedure. Once the plug is inserted, it is clearly visible, and the defibrillator should be handled accordingly.

It is noted that FIG. 1 shows only one case-activating connector cavity 26, having positive polarity, which has been found to be the most effective polarity for the active can. However, the negative lead connector cavity 22 may also be of this case-activating type having two conductive elements. This would provide the implanting physician with yet another option in electrode configuration choice.

Other options for connector cavity configuration within the header are possible. For example, the header may be made smaller by providing only two defibrillator connector cavities instead of three, with at least one of the two being of the caseactivating type described.

Figure 2:
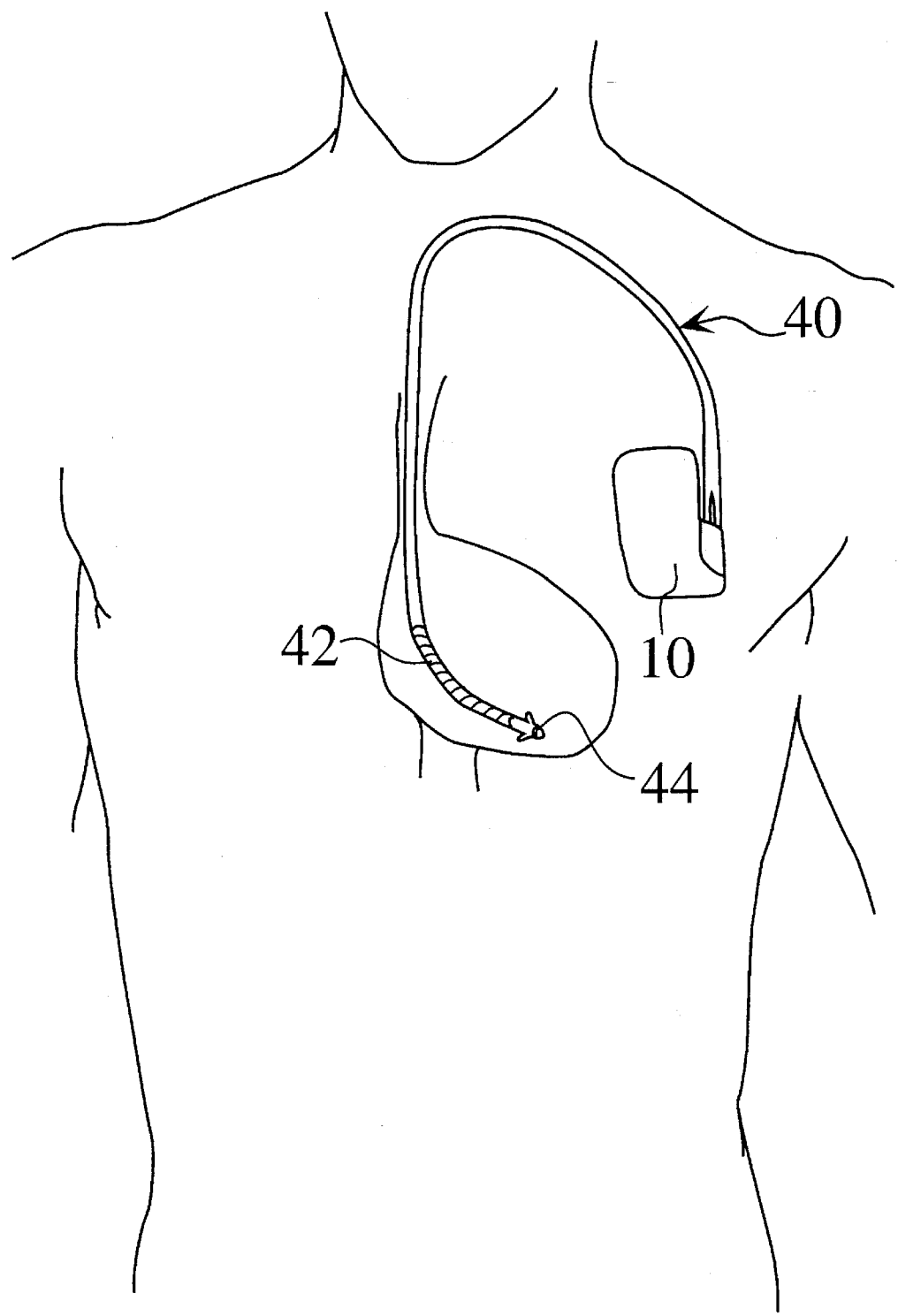
FIG. 2 illustrates the placement of an activated pulse generator case of the present invention in the patient's pectoral region adjacent the heart, connected to an implanted transvenous lead.

FIG. 2 illustrates the placement of the pulse generator 10 near the heart in the pectoral region of the patient. It is connected to an implanted transvenous lead 40, which has a pacing tip electrode 44 and one high surface area electrode 42 which is used alternately for defibrillation and for sensing. The electrodes are located in the right ventricle and the pulse generator 10 is located in the left pectoral region of the chest. Alternatively, the generator may be located at the level of the ventricles or in the abdominal region. The positive defibrillation lead connector cavity is plugged to prevent body fluids from entering it, using a plug similar to the one shown in FIG. 6. Alternatively, an electrode may be connected to this connector cavity.

It should also be noted that a defibrillator of the present invention may be used with preexisting leads. For example, if during a typical defibrillator replacement, due to end of battery life, the DFT is found to have increased in a patient having only RV and SVC electrodes, a replacement defibrillator with an active can as an additional electrode may be used with the existing leads to decrease the DFT.

Figure 3:
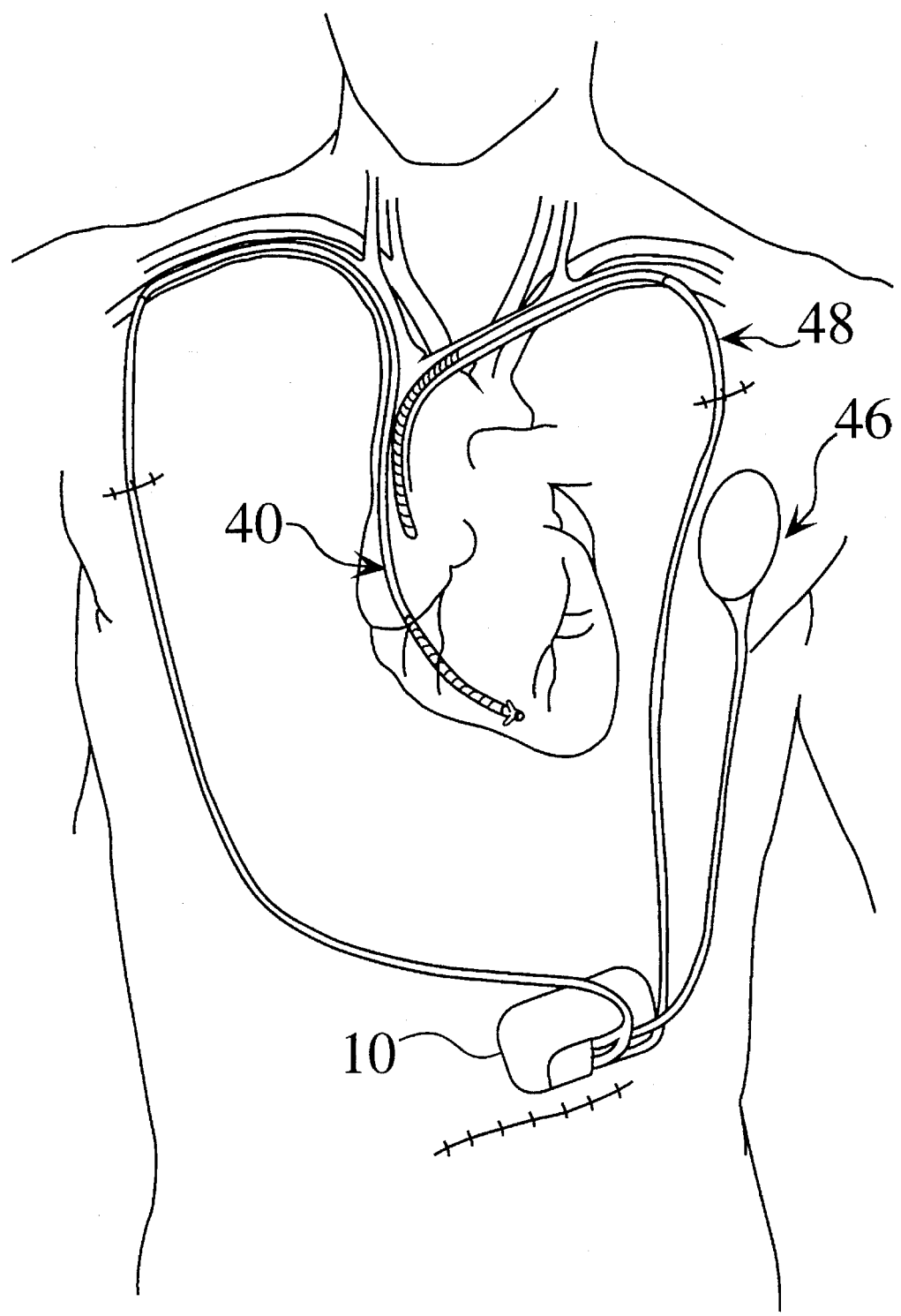
FIG. 3 illustrates the placement of an inactive pulse generator case of the present invention in the abdominal region, having a subcutaneous lead plugged into the case-activating connector cavity, and also connected to a right ventricular and a superior vena cava lead.

FIG. 3 illustrates the placement of a pulse generator 10 with an inactive case in the abdominal region, having a subcutaneous lead 46 implanted in the left chest wall and connected to the case activating connector cavity. Pulse generator 10 is also connected to a right ventricular lead 40 and a superior vena cava lead 48.

Referring back to FIG. 4, the conductive elements 34 and 36 of the caseactivating connector cavity 26 of FIG. 1 are shown, with a lead connector 50 inserted. Each conductive element 34 and 36 comprises a setscrew, 56 and 58 respectively. Before setscrews 56 and 58 are tightened, insulative separators, 60 and 62 electrically isolate conductive elements 34 and 36 respectively, from the lead connector pin or plug pin, and from each other. Insulative separators 60 and 62 are shown as elastomeric membranes which may be easily pierced by setscrews 56 and 58. Alternatively, the seal may be a viscous, nonconductive silicone grease, silicone gel, or the like. The grease or gel is displaced by the pin during pin insertion, but then reforms to block the conductive fluid path between the conductive elements 34 and 36 thereby achieving a fluid insulated connection. As another alternative, the seal may comprise an elastomeric membrane used in combination with a viscous, nonconductive grease. Setscrew 56 of conductive element 34 has been tightened down onto lead connector pin 52, piercing through insulative separator 60. The setscrew 58 of conductive element 36 has not been tightened; therefore insulative separator 62 remains intact. Thus, only the electrode attached to the lead connector pin 52 is active for defibrillation; the defibrillator case remains inactive.

FIG. 5 shows the conductive elements 34 and 36 of the case-activating connector cavity 26 of FIG. 1, with a case-activating plug 38 inserted. The setscrews 56 and 58 of both conductive elements 34 and 36 have been tightened down onto plug pin 54, piercing both insulative separators 60 and 62, electrically connecting the can to the positive defibrillator output of the pulse generator.

FIG. 6 shows the conductive elements 34 and 36 of the case-activating connector cavity 26 of FIG. 1, having a plug 38 to fill the cavity 26 but not activate the can. The pin 54 in this case is for making a mechanical connection to the cavity, and may be made of conductive or nonconductive material. As shown, only one setscrew has been tightened onto plug pin 54. This plug 38 prevents body fluids from entering the cavity, which keeps the cavity open for optional future use.

Figure 7:
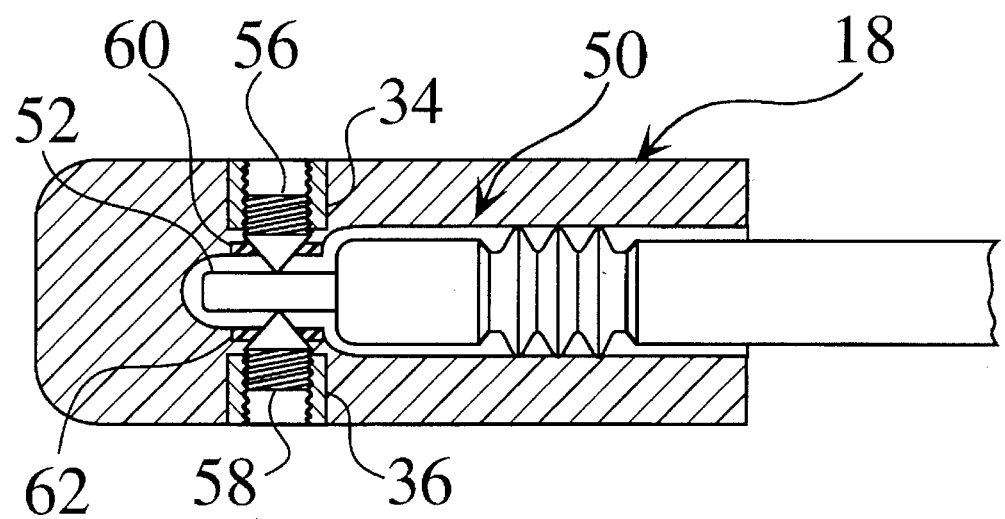
FIG. 7 is a top plan view partially cut away showing a connector assembly having the two connector blocks of the case-activating connector cavity of FIG. 1, having a lead inserted with both the lead and can activated.

FIG. 7 shows the conductive elements 34 and 36 of the case-activating connector cavity 26 of FIG. 1, having a lead connector 50 inserted which has had both setscrews 56 and 58 tightened onto the lead connector pin to activate both the lead and the can. In this embodiment, both the device housing and the electrode attached to the lead connector pin are of the same polarity.

Figure 8:
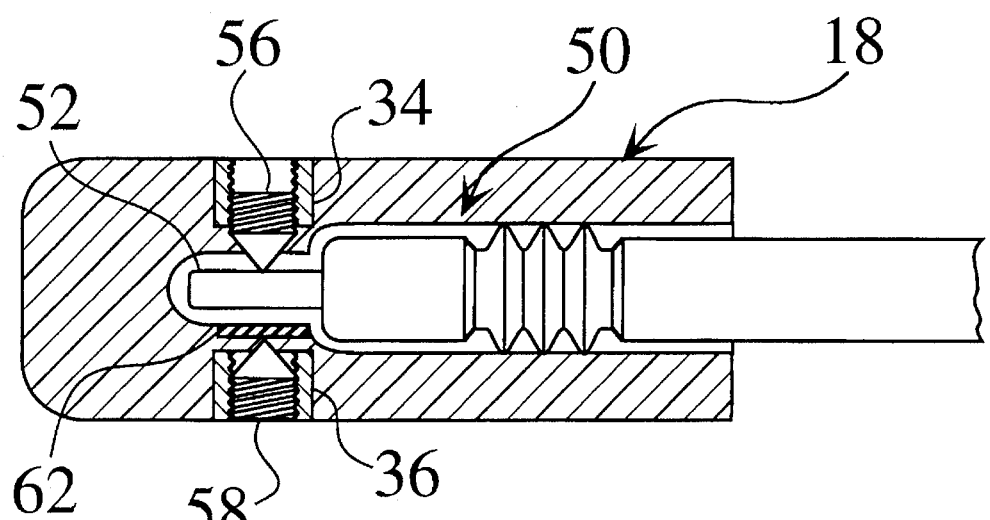
FIG. 8 is a top plan view partially cut away showing two connector blocks of a case-activating connector cavity with only one fluid seal.

FIG. 8 is a top plan view partially cut away showing two conductive elements 34 and 36 of a case-activating connector cavity having only one fluid seal 62. Tightening setscrew 56 onto a lead connector pin plugged into the cavity activates the lead; by not tightening setscrew 58, fluid seal 62 remains intact, and the defibrillator case remains electrically inactive. Tightening setscrew 56 onto a plug pin mechanically stabilizes the plug without activating the case. When setscrew 58 is also tightened onto a lead or plug pin, fluid seal 62 is pierced and the pin is electrically connected to the defibrillator case, thereby activating it for defibrillation.

Conductive elements 34 and 36 may alternatively be electrically isolated from each other by means of an air gap that is maintained when the setscrews are not tightened, thereby eliminating the need for fluid seal 62. Conductive body fluids may be kept out of the cavity simply by the seal formed by the lead or plug sealing rings against the connector cavity. An additional seal may be provided in the cavity that can be penetrated by the lead or plug connector pin, but that reseals against the pin once in place, similar to the seals disclosed in Pless et al. above. Note that if fluid seal 62 is eliminated, the electrically conductive element 36 must be offset from the connector pin portion of cavity 26, as electrically conductive elements 34 and 36 are shown, to prevent inadvertent direct contact of connector pin 52 to element 36.

Figure 9:
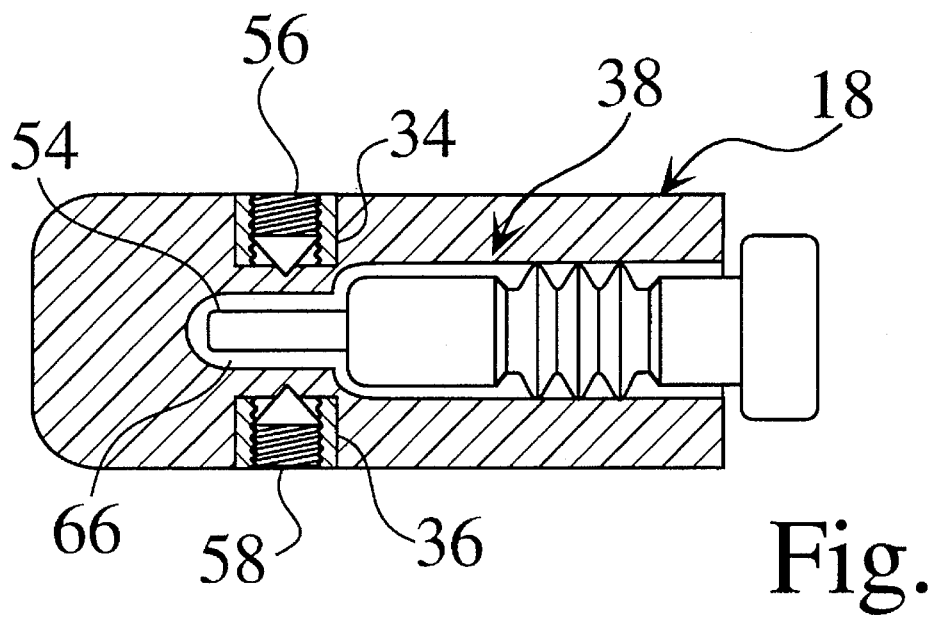
FIG. 9 illustrates the device of FIG. 8 wherein the conductive elements are electrically isolated from each other by means of an air gap that is maintained when the setscrews are not tightened.

FIG. 9 illustrates the device of FIG. 8 wherein the conductive elements are electrically isolated from each other by means of an air gap 66 that is maintained when the setscrews 56 and 58 are not tightened.

Figure 10:
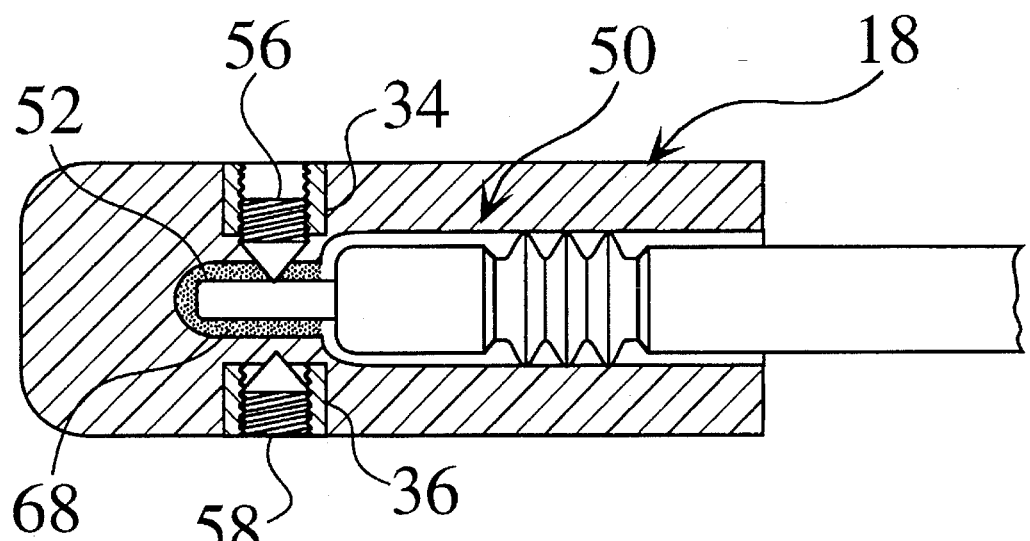
FIG. 10 illustrates a device of the present invention wherein the conductive elements are electrically separated by a viscous material.

FIG. 10 illustrates a device of the present invention wherein the conductive elements 34 and 36 are electrically separated by a viscous material 68 The seal may be a viscous, nonconductive silicone grease, silicone gel, or the like. The grease or gel is displaced by the pin during pin insertion, but then reforms to block the conductive fluid path between the conductive elements 34 and 36 thereby achieving a fluid insulated connection. An elastomeric membrane may be used in combination with the viscous, nonconductive grease.

Figure 11:
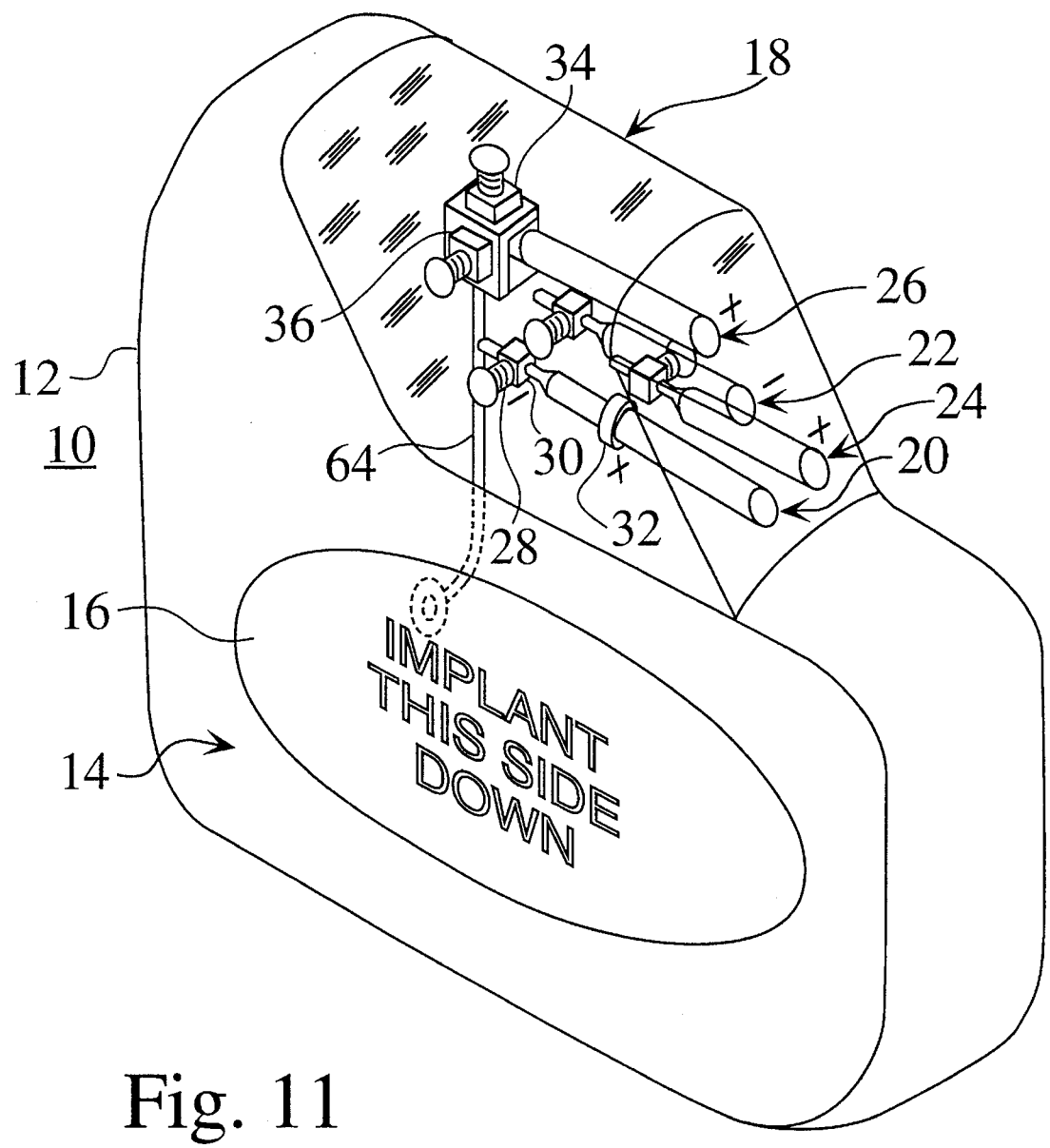
FIG. 11 illustrates a device of the present invention having conductive elements positioned 90 degrees apart.

FIG. 11 illustrates a device of the present invention having conductive elements 34 and 36 positioned 90 degrees apart.

It should be understood that various alternatives to the embodiments of the invention described herein may be employed in practicing the invention. It is thus intended that the following claims define the scope of the invention and that structures and methods within the scope of these claims and their equivalents be covered thereby.

What is claimed is:

1. An implantable cardiac stimulator comprising:

a pulse generator case having an electrically conductive portion;

pulse generator circuitry housed in said case;

a header attached to said case, said header including at least first and second connector cavities;

said first connector cavity having a first conductive element electrically coupled to said pulse generator circuitry; and said second connector cavity having an entrance end and a perimeter, and having a first conductive element located at a first distance from said entrance end and at a first position on said perimeter and electrically coupled to said pulse generator circuitry, and having a second conductive element electrically connected to said electrically conductive portion of said case and located at a second position on said perimeter circumferentially spaced from said first position.

2. The implantable cardiac stimulator of claim 1 wherein each of said second connector cavity conductive elements comprises a connector block having a setscrew.

3. The implantable cardiac stimulator of claim 1 wherein said first position and said second position are about 180° apart on said perimeter.

4. The implantable cardiac stimulator of claim 1 wherein said first position and said second position are about 90° apart on said perimeter.

5. The implantable cardiac stimulator of claim 1 wherein said second cavity second conductive element is located at a second distance from said entrance end wherein said second distance is approximately equal to said first distance from said entrance end.

6. The implantable cardiac stimulator of claim 1 wherein said second cavity second conductive element is located at a second distance from said entrance end wherein said second distance is within 5 mm of said first distance from said entrance end.

7. The implantable cardiac stimulator of claim 1, and further comprising a fluid seal between said second cavity first and second conductive elements.

8. The implantable cardiac stimulator of claim 7, wherein said fluid seal comprises an elastomeric membrane completely separating said second cavity first and second conductive elements.

9. The implantable cardiac stimulator of claim 7, wherein said fluid seal comprises a viscous, nonconductive, fluid-impervious material.

10. The implantable cardiac stimulator of claim 1 wherein said first cavity conductive element and said second cavity conductive elements are of opposite polarity.

11. The implantable cardiac stimulator of claim 1, wherein said header further includes a pacing lead connector cavity electrically connected to said pulse generator circuitry.

12. The implantable cardiac stimulator of claim 1 wherein said first cavity further includes a second conductive element electrically connected to at least a portion of said pulse generator case, and having a fluid seal between said first cavity first and second conductive elements.

13. The implantable cardiac stimulator of claim 1 wherein said pulse generator case is partially encapsulated by a polymeric insulating coating.

14. An implantable cardiac defibrillator system comprising:

a pulse generator case having an electrically conductive portion and adapted for subcutaneous implantation either pectorally, abdominally, or at the level of the ventricles of a patient's heart;

defibrillation pulse generator circuitry housed in said case;

a header attached to said case, said header including at least first and second connector cavities;

a transvenous lead having a defibrillation lead connector pin inserted into said first connector cavity;

a device inserted into said second connector cavity, said device including a device pin;

said first connector cavity having a conductive element of a first polarity for making electrical connector contact to said defibrillation lead connector pin;

said second connector cavity having an entrance end and a perimeter, and having a first conductive element of a second polarity for making electrical contact to said device pin, and being located at a first distance from said entrance end and at a first position on said perimeter, and a second conductive element electrically connected to said electrically conductive portion of said case, located at a second position on said perimeter circumferentially spaced from said first position, and being movable into a first arrangement in contact with said device pin and into a second arrangement not in contact with said device pin; and means for electrically isolating said second connector cavity second conductive element from said second connector cavity first conductive element when said second cavity second conductive element is in said first arrangement and for allowing electrical conduction between said second connector cavity first conductive element and said second connector cavity second conductive element when said second cavity second conductive element is in said second arrangement.

15. The implantable cardiac defibrillator system of claim 14, wherein said means for electrically isolating comprises an elastomeric membrane penetrated by said second connector cavity second conductive element when said second cavity second conductive element is in said second arrangement.

16. The implantable cardiac defibrillator system of claim 14, wherein said means for electrically isolating comprises a viscous, nonconductive, fluid-impervious material penetrated by said second connector cavity second conductive element when said second cavity second conductive element is in said second arrangement.

17. The implantable cardiac defibrillator system of claim 14, wherein said means for electrically isolating comprises an air gap between said second connector cavity first and second conductive elements maintained when said second cavity second conductive element is in said first arrangement.

18. The implantable cardiac stimulator of claim 14 wherein said device is a plug comprising said device pin, and an insulative body portion.

19. The implantable cardiac stimulator of claim 14 wherein said device comprises a defibrillation lead connector including said device pin and further including an insulative connector body portion, wherein said defibrillation lead connector is coupled to a defibrillation electrode.

20. An implantable cardiac defibrillator system kit comprising:

a pulse generator case having an electrically conductive portion and adapted for subcutaneous implantation either pectorally, abdominally, or at the level of the ventricles of a patient's heart;

defibrillation pulse generator circuitry housed in said case;

a header attached to said case, said header including at least first and second connector cavities;

a transvenous lead having a defibrillation lead connector pin adapted to be inserted into said first connector cavity;

a device adapted to be inserted into said second connector cavity, said device including a device pin;

said first connector cavity having a conductive element of a first polarity capable of making electrical connector contact to said defibrillation lead connector pin when said defibrillation lead connector pin is inserted into said first connector cavity;

said second connector cavity having an entrance end and a perimeter, and having a first conductive element of a second polarity capable of making electrical contact to said device pin when said device is inserted in said second connector cavity, and being located at a first distance from said entrance end and at a first position on said perimeter, and a second conductive element electrically connected to said electrically conductive portion of said case, located at a second position on said perimeter circumferentially spaced from said first position, and being movable into a first arrangement in contact with said device pin and into a second arrangement not in contact with said device pin; and means for electrically isolating said second connector cavity second conductive element from said second connector cavity first conductive element when said second cavity second conductive element is in said first arrangement and for allowing electrical conduction between said second connector cavity first conductive element and said second connector cavity second conductive element when said second cavity second conductive element is in said second arrangement.

\* \* \* \* \*